Figure 1:
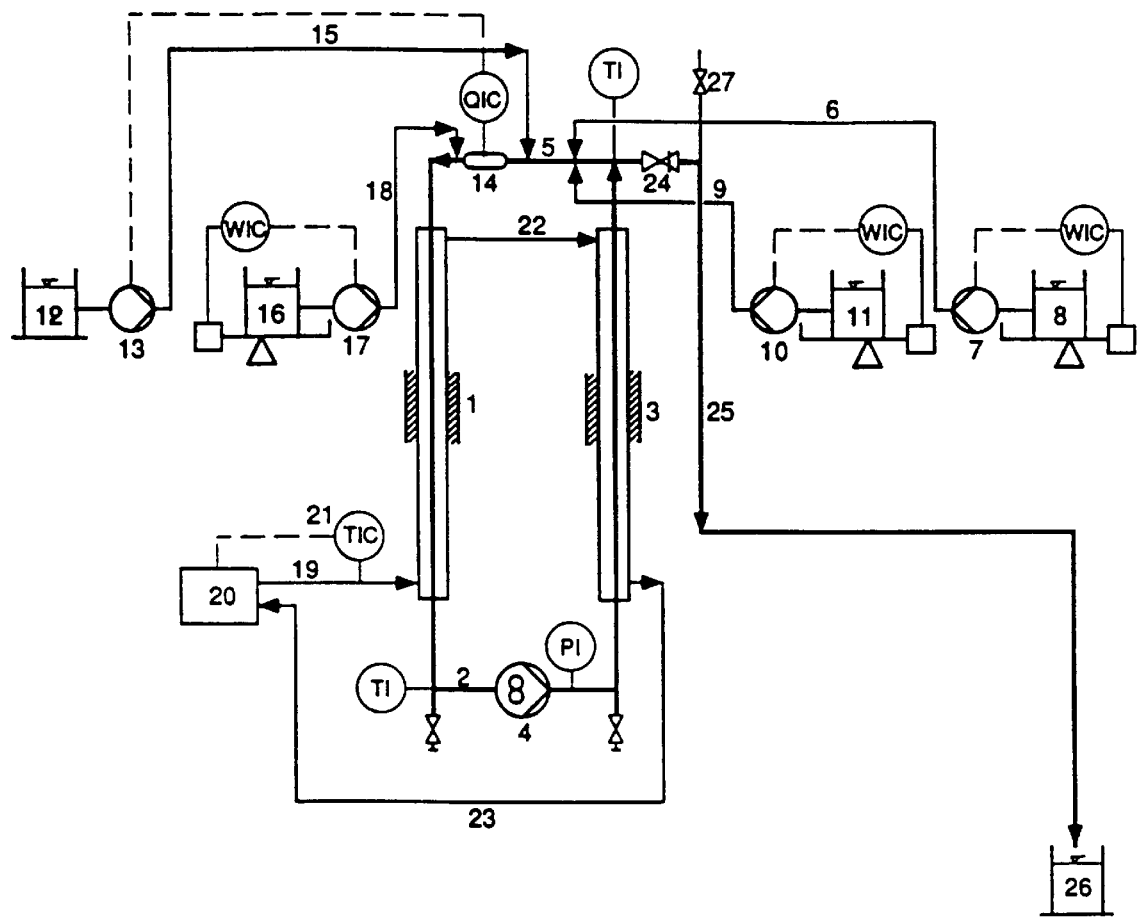

United States Patent

Ehle et al.

Patent Number: 5,942,635
Date of Patent: Aug. 24, 1999

[54] CONTINUOUS PREPARATION OF N-ACYLAMINO CARBOXYLIC ACIDS AND N-ACYLAMINO SULPHONIC ACIDS, AND THEIR ALKALI METAL SALTS

[75] Inventors: Beate Ehle; Georg Schuh; Martin aus dem Kahmen, all of Ludwigshafen; Dieter Hertel, Leimen, all of Germany

[73] Assignee: BASF Aktiengesellschaft, Ludwigshafen, Germany

[21] Appl. No.: 09/068,012
[22] PCT Filed: Oct. 30, 1996
[86] PCT No.: PCT/EP96/04723
§ 371 Date: Apr. 30, 1998
§ 102(e) Date: Apr. 30, 1998
[87] PCT Pub. No.: WO97/16409
PCT Pub. Date: May 9, 1997

[30] Foreign Application Priority Data

Oct. 31, 1995 [DE] Germany ............... 195 40 645

[51] Int. Cl.⁶ .................................................. C07C 231/00
[52] U.S. Cl. ........................................ 554/69; 562/575
[58] Field of Search ............................. 554/69; 562/575

[56] References Cited

U.S. PATENT DOCUMENTS

| | | |
|---|---|---|
| 3,544,606 | 12/1970 | Singer, Jr. et al. . |
| 4,095,952 | 6/1978 | Schmidt et al. . |
| 4,278,539 | 7/1981 | Santhanam et al. . |
| 5,646,319 | 7/1997 | Letton et al. ............ 554/69 |
| 5,710,295 | 1/1998 | Woodbury et al. ........ 554/69 |
| 5,856,538 | 1/1999 | Strecker et al. .......... 554/63 |

FOREIGN PATENT DOCUMENTS

| | | |
|---|---|---|
| 0 033 392 | 12/1980 | European Pat. Off. . |
| 0 510 596 | 10/1992 | European Pat. Off. . |
| 1 465 959 | 1/1966 | France . |
| 2 424 287 | 11/1979 | France . |
| 85 757 | of 0000 | Germany . |
| 635 522 | 9/1936 | Germany . |
| 1 493 650 | 8/1963 | Germany . |
| 1 618 097 | 2/1967 | Germany . |
| 2004 099 | 1/1970 | Germany . |
| 14 93 660 | 2/1972 | Germany . |
| 131 467 | 6/1977 | Germany . |
| 692 568 | 6/1953 | United Kingdom . |

OTHER PUBLICATIONS

Chemical Abstracts, vol. 93, No. 16, Oct. 20, 1980, Kajl, Marian et al.
Chemical Abstracts, vol. 122, No. 5, Jan. 1995 is equivalent to JP 06 256 276.
J. Am Chem Soc. 78(1956), 1721, E. Jungermann et al.

*Primary Examiner*—Samuel Barts
*Attorney, Agent, or Firm*—Oblon, Spivak, McClelland, Maier & Neustadt, P.C.

[57] ABSTRACT

In a process and an apparatus for the continuous preparation of N-acylamino carboxylic acids and N-acylamino sulfonic acids, and their alkali metal salts, from the alkali metal salts of amino carboxylic acids and amino sulfonic acids, respectively, and carbonyl halides in a reactor designed as circulating circuit, the reactants are fed for immediate reaction into the circulating circuit, and a part of the product solution corresponding to the amount fed in is continuously discharged from the circulating circuit. The reactants are circulated by a circulating pump. The temperature in the reactors is controlled. The heat produced in the reaction is removed.

4 Claims, 1 Drawing Sheet

CONTINUOUS PREPARATION OF N-ACYLAMINO CARBOXYLIC ACIDS AND N-ACYLAMINO SULPHONIC ACIDS, AND THEIR ALKALI METAL SALTS

This application is a 371 of PCT/EP96/04723 filed Oct. 30, 1996.

The invention relates to a process and an apparatus for the continuous preparation of N-acylamino carboxylic acids and N-acylamino sulfonic acids, and their alkali metal salts, from the alkali metal salts of amino carboxylic acids and amino sulfonic acids, respectively, and carbonyl halides in a reactor designed as circulating circuit.

Various synthetic routes are known for preparing long-chain acylamino acids from fatty acid derivatives and amino acids, and they differ essentially in the acylation component used. Although fatty acids (DE-A 20 04 099) and fatty acid methyl esters (EP-A 0 033 392) are suitable in principle as acylation component, they have not to date been able to achieve industrial significance.

A process utilized industrially for preparing long-chain N-acylamino acids is condensation of fatty acid chlorides with amino acids, with elimination of hydrochloric acid, also known as the Schotten-Baumann reaction. This process has been known for a long time (DE-C 635 522) and is utilized commercially, for example to prepare oleoylsarcosine, also known under the name "Medialan acid", which is used in particular as corrosion inhibitor, fuel additive and in water repellants for leather.

The general principle for synthesizing Medialan acid, other acylsarcosinates and compounds of related structure (E. Jungermann et al., J. Amer. Chem. Soc. 78 (1956) 172 f; U.S. Pat. No. 3,544,606, FR-B 1 465 959, DD-C 85 757, DE-A 14 93 650, DE-A 16 18 097) comprises initially introducing the amino acid as Na salt in aqueous solution and in metering in, while stirring, the fatty acid chloride and NaOH sufficiently slowly to keep the temperature at below 35° C. and the pH at 9–12.5. After the addition is complete, the pH of the reaction mixture is adjusted to <5 by adding $H_2SO_4$. The acylamino acid obtained in this way is separated off as organic phase, where appropriate with the addition of an organic solvent to induce phase separation, which is subsequently removed again under reduced pressure. If the alkali metal salt of the acylamino acid is required, the acylamino acid is taken up in water and neutralized by adding NaOH. There have been numerous publications on the optimization of the individual process steps and reaction parameters, eg. the phase separation or the hydrolysis rate as a function of the pH and temperature.

The reaction of fatty acid halides with amino acid salts, which appears very straightforward at first sight, involves some critical points to which careful attention must be paid in order to be able to prepare acylamino acids in good yield and high purity. Since the reaction is very fast, when the two reactants are efficiently mixed the reaction is complete in <1 min. Thus, in the alkaline range (pH >8), the acylation reaction is distinctly faster (about 100 times) than the competing hydrolysis of the fatty acid chloride. The two reactions take place at approximately the same rate in an acidic medium. Raising the temperature increases the rate of hydrolysis more than that of condensation. Furthermore, the acylation reaction is highly exothermic, which means that the difference in the reaction rate can be utilized only if it is possible to remove the heat evolved in the reaction quickly enough. Since a dilute aqueous medium is used, the reaction mixture may be prone to foaming (surfactant).

Conventional stirred vessel technology carried out batchwise is in principle suitable for preparing acylamino acids, but has some disadvantages which eventually have adverse effects on the product quality. These disadvantages are: difficulty of controlling the temperature and removing the heat, furthermore relatively long holdup times per batch according to the quantity in the batch. As the reaction progresses, the properties of the reaction mixture, eg. concentration, volume, viscosity, change and thus so too do the variables determining the reaction rate.

It has therefore also been suggested to provide a remedy by a continuous synthesis. Thus, it is known (DE-A 14 93 660) for continuous reaction of fatty acid chlorides with amino carboxylic acids or amino sulfonic acids or their soluble salts to use for the mixing and reacting mixing equipment which consists of fixed and rotating parts with cylinders, cones, disks or rings, which are provided with serrations, perforations or with pins and similar elements, on the rotating part and/or the fixed part. The disadvantage is that such rotor/stator systems comprise very elaborate and costly apparatus. Efficient removal of heat as far as the low temperature region (30–40° C. as is beneficial, for example, for oleoylsarcosine) is difficult, especially since additional energy input takes place due to the high shear forces.

M. Kajl et al., Tenside Detergents 17 (1980) 174 f. suggest the use of a nozzle reactor for efficient mixing of the reactants. This has the disadvantage that control of the removal of heat in the nozzle reactor is possible only with difficulty. It is therefore necessary to have a downstream cooling section, and local temperature peaks may occur. Furthermore, foaming must be expected. It is also known (DD-C 131467) for vigorous mixing to introduce the reactant streams close to one another and directly below a stirring system into a stirred container. The disadvantages associated with this are the same as with batchwise stirred vessel technology.

It is an object of the present invention to find a process for the continuous reaction of fatty acid halides with amino carboxylic acids and amino sulfonic acids or their salts which provides acylamino acids in high yield and purity, continuously, in large quantities, in a simple, economical and versatile apparatus, with efficient removal of heat, without foaming problems and under constant conditions.

We have found that this object is achieved by a process for the continuous preparation of N-acylamino carboxylic acids and N-acylamino sulfonic acids, and their alkali metal salts, from the alkali metal salts of amino carboxylic acids and amino sulfonic acids, respectively, and carbonyl halides in a reactor designed as circulating circuit, in which the reactants are fed for immediate reaction into the circulating circuit, and a part of the product solution corresponding to the amount fed in is continuously discharged from the circulating circuit. In an advantageous embodiment of the invention, the heat produced during the reaction is removed.

The reactants can advantageously be circulated by a circulating pump. The temperature in the reactors is controlled. An alkaline solution is metered under pH control into the circulation circuit to maintain a constant pH. In addition, when required, an organic agent to induce phase separation and/or a foam suppressant is fed into the reaction circulation.

It has been found, that turbulent flow in a simple pipe is sufficient to achieve efficient mixing of the fatty acid halide and amino acid salt solution and thus to utilize the speed of the reaction.

Furthermore this object is achieved by an apparatus for carrying out the process, wherein a reactor consisting of pipes arranged in series, with integrated circulating pump is provided, and its outlet end is connected by a pipe to its inlet end, and wherein the reactor is provided with supply lines for the reactants and with an overflow valve for the reaction product.

The process according to the invention can be applied to the preparation of N-acylamino carboxylic acids and N-acylamino sulfonic acids, and their alkali metal salts, from the alkali metal salts of amino carboxylic acids and amino sulfonic acids, respectively, and carbonyl halides particularly well when the alkali metal salts of amino carboxylic acids which are used are the lithium, sodium or potassium salts of aliphatic amino carboxylic acids with 2 to 10 carbon atoms, preferably 3 to 6 carbon atoms, in particular of valine, leucine, norleucine, glycine, alanine, β-alanine, ε-aminocaproic acid, α-aminoisobutyric acid, sarcosine (N-methylglycine), aspartic acid, glutamic acid or iminodiacetic acid. However, it is also possible to use the sodium or potassium salts of other natural α-amino acids, of oligopeptides or of aromatic or cycloaliphatic amino carboxylic acids, eg. anthranilic acid, phenylglycine, phenylalanine or 1-aminocyclohexane-1-carboxylic acid. It is immaterial in this connection whether the alkali metal salts of the amino carboxylic or sulfonic acids are used as such or are produced from the corresponding amino acids in the alkaline reaction medium.

By amino carboxylic acids are meant in this connection in particular compounds with a primary or secondary amino group and one or two carboxyl groups per molecule; however, it is also possible in principle for compounds with more than one amino group and/or more than two carboxyl groups to be used, and then the quantity of carbonyl halides depends on the number of amino groups. All carboxyl groups are present virtually completely in the salt form.

The process according to the invention can likewise be used particularly well when the alkali metal salts of amino sulfonic acids which are used are the lithium, sodium or potassium salts of aliphatic amino sulfonic acids with 2 to 10 carbon atoms, preferably 2 to 4 carbon atoms. Of particular interest in this connection are the corresponding salts of taurine (2-amino-ethanesulfonic acid) and N-methyltaurine. Just like the amino carboxylic acids, it is possible for the amino sulfonic acids used, which are likewise present virtually completely in the alkali metal salt form, to have a plurality of amino groups and/or sulfo groups.

Particularly suitable carbonyl halides are fatty acid chlorides and bromides, i.e. chlorides and bromides of saturated or unsaturated $C_6$–$C_{30}$-monocarboxylic acids. Especially suitable are the saturated or mono- to polyunsaturated $C_8$–$C_{20}$-monocarboxylic acids, eg. lauric acid, myristic acid, palmitic acid, stearic acid, oleic acid, linoleic acid or linolenic acid, or mixtures of such naturally occurring long-chain fatty acids, eg. coconut fatty acid, palm oil fatty acid, palm kernel oil fatty acid, tallow fatty acid, soybean oil fatty acid, linseed oil fatty acid, canola fatty acid, sunflower oil fatty acid or rapeseed oil fatty acid, and corresponding synthetic $C_8$–$C_{20}$-monocarboxylic acids or mixtures thereof.

Agents which can be used to induce phase separation are ketones (such as methyl ethyl ketone, isopropyl methyl ketone, acetone), esters (such as ethyl acetate, methyl acetate, ethyl propionate, methyl propionate, isopropyl acetate and other alkyl or aryl carboxylates), alcohols (such as propanol, isopropanol, n-butanol, 2-butanol, isobutanol), dialkyl ethers (such as diethyl ether, methyl tert-butyl ether, diisopropyl ether) and other compounds known in the prior art to be suitable for this purpose.

The drawing as enclosed shows in FIG. 1 a flow diagram describing how the process according to the present invention is conducted and describing the respective apparatus.

Further details and advantages of the invention can be found in the exemplary embodiment described by means of the flow diagram depicted in the drawing. In this connection, the functional principle will first be explained generally taking the example of the preparation of oleoylsarcosine.

The reactor for carrying out the process according to the invention consists of a pump circulating circuit. The circulation line of the reactor consists of various pipe sections 1, 2, 3, 5. Oleoyl chloride is metered from a tank 8 with pump 7 through feed line 6, and sarcosine sodium solution is metered from tank 11 with pump 10 through line 9, in each case in a rate-controlled manner to the reactor. Circulating pump 4 maintains the circulation flow within the reactor. This pipe flow ensures efficient mixing of the reactants. For systems with pipes of larger cross-section, the pipes can be equipped with internals such as static mixers, packings or other apparatus/internals suitable for intensifying the mixing. Alkaline solution, e.g. aqueous NaOH solution is metered from a tank 12 by means of a pump 13 with the aid of a pH-measuring probe 14 through line 15 so that a constant pH in the reaction mixture is maintained. Furthermore, if required, an other reaction aid such as an organic agent which induces phase separation, e.g. methyl ethyl ketone, is fed from a tank 16 by a pump 17 through a line 18 under rate control. The residence time in the pump circulation can be controlled by the metering rate, and the mixing by altering the circulation flow. Since the circulation comprises a system which is completely filled with liquid, no foaming of the aqueous surfactant mixture occurs.

The temperature in the pump circulation is controlled. This is preferably conducted in a way that at least one part of the reactor can be cooled, especially the parts of the reactor located upstream and downstream of the circulating pump 4. The heat removal takes place by pipe sections 1 and 3 which are each equipped with a jacket. Cooling fluid flows through these jackets via line 19, 22 and 23. The temperature of the cooling medium can be adjusted depending on the required product temperature. The appropriate control system obtains the particular actual value of the coolant initial feed temperature via the temperature sensor 21 which is designated TIC. Adjustment takes place by means of thermostat 20. Control via direct measurement of the product temperature is possible. The removal of the heat of reaction in larger systems can likewise take place by incorporating a conventional heat exchanger, such as a plate heat exchanger, tube bundle heat exchanger or similar apparatus, into the pipeline designed as circulating circuit. The cooling liquid flows, after leaving the cooling jacket of section 1, through a line 22 into the cooling jacket of section 3 and from the latter through line 23 back to the thermostat 20. Continuous discharge of a part-stream of product from the pump circulation takes place through an overflow valve 24 via discharge line 25, which terminates in a tank 26. A ventilation line 27 is connected to discharge line 25. TI in the drawing designates further temperature sensors, and PI designates a pressure sensor, WIC and QIC are defined as weight indication and quantity indication control.

The volume of the pump circulation through the reactor in the apparatus used for carrying out Examples 1–3 was 170 ml. The dimensions of the reactor pipes 1 and 3 were Ø 12×1×1000 mm.

The metering and the product discharge take place continuously and can be controlled by a process control system. If the system is in equilibrium, the acylation reaction always takes place in a reaction medium of constant composition. That is to say parameters relevant to the reaction, such as viscosity, concentration etc., do not change. This means that the heat transfer also remains constant, which ensures uniform, very readily controllable removal of heat.

This continuous acylation is followed by neutralization, phase separation and removal of the organic solvent; which can be conducted in a way that the product stream leaving the reactor is passed through further reactors for subsequent or further reaction. These can likewise be carried out continuously in a conventional manner. This may entail the neutralization taking place in a mixing section, the phase separation taking place in a simple settler system and the removal of the solvent taking place in evaporators.

The following experimental examples of the synthesis of N-oleoylsarcosine were carried out with the experimental arrangement described above.

EXAMPLE 1

The volume of the pump circuit (170 ml) is filled with water or an aqueous solution of oleoylsarcosine Na and methyl ethyl ketone.

At a temperature of 40° C., 206 g/h water, 211 g/h of a sarcosine Na solution (40.1% strength), 229 g/h oleoyl chloride and 94 g/h methyl ethyl ketone are fed in simultaneously. The pH is measured by the pH electrode incorporated in the circulation, and the pH is kept constant at from 10 to 10.5 by adding 10% strength sodium hydroxide solution.

Part of the finished crude product is discharged continuously from the pump circuit through the overflow valve as aqueous suspension in water and methyl ethyl ketone together with the NaCl produced (dissolved in the suspension). The circulating pump which pumps the reaction mixture in the circuit is adjusted so that a flow rate of 1200 ml/min is reached. The average residence time is 10 minutes.

For workup, the crude mixture discharged from the pump circuit is then continuously adjusted to pH 1–1.5 by adding concentrated sulfuric acid. Phase separation takes place in a downstream phase separator. The organic phase is passed through a falling film evaporator to remove the agent to induce phase separation (methyl ethyl ketone).

Free oleoylsarcosine acid is obtained as pale yellow oil (255 g/h) with a content of 96.4% by weight oleoylsarcosine acid and 3.6% by weight oleic acid.

EXAMPLE 2

The volume of the pump circuit (170 ml) is filled with water or an aqueous solution of oleoylsarcosine Na and methyl ethyl ketone.

At a temperature of 40° C., 425 g/h water, 235 g/h of a sarcosine Na solution (40.1% strength), 213 g/h oleoyl chloride and 91 g/h methyl ethyl ketone are fed in simultaneously. The pH is measured by the pH electrode incorporated in the circulation, and the pH is kept constant at from 10 to 10.5 by adding 50% strength sodium hydroxide solution.

Part of the finished crude product is discharged continuously from the pump circuit through the overflow valve as aqueous suspension in water and methyl ethyl ketone together with the NaCl produced (dissolved in the suspension). The circulating pump which pumps the reaction mixture in the circuit is adjusted so that a flow rate of 1200 ml/min is reached. The average residence time is 10 minutes.

For workup, the crude mixture is then in a buffer tank adjusted to pH 1–1.5 by adding concentrated sulfuric acid. Continuous phase separation takes place in a downstream phase separator. The organic phase is passed through a falling film evaporator to remove the agent to induce phase separation (methyl ethyl ketone).

Free oleoylsarcosine acid is obtained as pale yellow oil (248 g/h) with a content of 96.5% by weight oleoylsarcosine acid and 3.5% by weight oleic acid.

EXAMPLE 3

The volume of the pump circuit (170 ml) is filled with water or an aqueous solution of oleoylsarcosine Na and methyl ethyl ketone.

At a temperature of 30° C., 438 g/h water, 211 g/h of a sarcosine Na solution (40.1% strength), 220 g/h oleoyl chloride and 94 g/h methyl ethyl ketone are fed in simultaneously. The pH is measured by the pH electrode incorporated in the circulation, and the pH is kept constant at from 10 to 10.5 by adding 50% strength sodium hydroxide solution.

Part of the finished crude product is discharged continuously from the pump circuit through the overflow valve 24 as aqueous suspension in water and methyl ethyl ketone together with the NaCl produced (dissolved in the suspension). The circulating pump which pumps the reaction mixture in the circuit is adjusted so that a flow rate of 1200 ml/min is reached. The average residence time is 10 minutes.

For workup, the crude mixture is then con-tinuously adjusted to pH 1–1.5 by adding concentrated sulfuric acid. Continuous phase separation takes place in a downstream phase separator. The organic phase is passed through a falling film evaporator to remove the agent to induce phase separation (methyl ethyl ketone).

Free oleoylsarcosine acid is obtained as pale yellow oil (252 g/h) with a content of 92% by weight oleoylsarcosine acid and 5.2% by weight oleic acid.

COMPARATIVE EXAMPLE C1

Batchwise preparation of oleoylsarcosine in a 1000 ml stirred apparatus 275 ml of water are introduced into a 1000 ml stirred apparatus, and 138.5 g of sarcosine Na solution (40.1% strength in water) and 65 g of methyl ethyl ketone are added. Subsequently, at 30° C., 151.8 g of oleoyl chloride and 40.5 g of a 50% strength sodium hydroxide solution are simultaneously added dropwise in such a way that the temperature is kept at 30° C. and the pH of the reaction mixture at 10–10.5. After the addition is complete (about 30 min), the pH of the reaction mixture is adjusted to 1.5 with 35 g of concentrated sulfuric acid. The organic phase is separated from the aqueous phase in a separating funnel, and the solvent is removed in a rotary evaporator under reduced pressure at about 50° C. (taking about 60 min).

164.9 g of an orange-yellow oil are obtained. N-Oleoylsarcosine content: 92.5%.

Comparison of Examples 1–3 according to the invention with Comparative Example C1 carried out as in the prior art shows that considerably higher yields per unit time and volume can be obtained with the process according to the invention than is the case with the known procedure.

The acylation stage in the Comparative Example was carried out in a reactor with a volume of 1000 ml. 164.9 g of product were prepared in 90 minutes.

Examples 1–3 were carried out in a reactor with a volume of 170 ml. About 255 g of product were prepared per hour.

This means that it is possible with the process according to the invention to prepare oleoylsarcosine in more than twice the amount per unit time and more than nine times the amount per unit volume, and thus a process with which acylsarcosine and other acylamino acids can be prepared in a good space/time yield even on the industrial scale is available.

It was furthermore possible to show with Examples 1–3 that oleoylsarcosine can be obtained in very good yield and high purity with the process according to the invention.

We claim:

1. A process for the continuous preparation of N-acylamino carboxylic acids and N-acylamino sulfonic acids, and their alkali metal salts, from the alkali metal salts of amino carboxylic acids and amino sulfonic acids, respectively, and carbonyl halides in a reactor designed as circulating circuit, wherein the reactants are fed for immediate reaction into the circulating circuit, and a part of the product solution corresponding to the amount fed in is continuously discharged from the circulating circuit, wherein the reactants are circulated by a circulating pump, the heat produced in the reaction is removed, and the temperature in the reactor is controlled.

2. A process as claimed in claim 1, wherein an alkaline solution is metered under pH control into the circulating circuit to maintain a constant pH.

3. A process as claimed in claim 1, wherein an organic agent to induce phase separation is fed into the circulating circuit.

4. A process as claimed in claim 1, wherein the product stream leaving the reactor is passed through further reactors for subsequent or further reaction.

* * * * *